(12) United States Patent
Farrell

(10) Patent No.: US 6,637,436 B2
(45) Date of Patent: Oct. 28, 2003

(54) ORAL APPLIANCE SUITABLE FOR USE AS A SPORTS GUARD

(76) Inventor: Christopher John Farrell, 1st Floor, Helensvale Plaza, Sir John Overall Drive, Helensvale, QLD 4210 (AU)

(*) Notice: Subject to any disclaimer, the term of this patent is extended or adjusted under 35 U.S.C. 154(b) by 0 days.

(21) Appl. No.: 10/232,240

(22) Filed: Aug. 30, 2002

(65) Prior Publication Data

US 2003/0019497 A1 Jan. 30, 2003

Related U.S. Application Data

(63) Continuation-in-part of application No. 10/070,349, filed as application No. PCT/AU99/00840 on Sep. 29, 1999.

(51) Int. Cl.[7] .................................................. A61C 5/14
(52) U.S. Cl. ........................................ 128/861; 128/862
(58) Field of Search ................................ 128/846, 848, 128/859–862; 433/6

(56) References Cited

U.S. PATENT DOCUMENTS 5,031,638 A * 7/1991 Castaldi ...................... 128/862
5,082,007 A * 1/1992 Adell ......................... 128/861
5,092,346 A 3/1992 Hays et al.
5,406,963 A 4/1995 Adell
5,566,684 A 10/1996 Wagner
5,826,581 A 10/1998 Yoshida

FOREIGN PATENT DOCUMENTS

| CA | 2024799 | 7/1991 |
| EP | 801937 A | 10/1997 |
| FR | 2639531 A | 6/1990 |
| WO | WO 93/08761 | 5/1993 |

* cited by examiner

Primary Examiner—Michael A. Brown
(74) Attorney, Agent, or Firm—Caesar, Rivise, Bernstein, Cohen & Pokotilow, Ltd.

(57) ABSTRACT

A sports guard for fitting over the upper arch and teeth of a user is disclosed. The sports guard comprises broadly a base member of polyethylene and a layer of EVA encasing the polyethylene. The polyethylene and EVA show a surprising and unexpected affinity for each other. They are able to flex with each other and be heated and cooled without delaminating. This provides a solution to a longstanding problem in this art.

9 Claims, 14 Drawing Sheets

ORAL APPLIANCE SUITABLE FOR USE AS A SPORTS GUARD

RELATED APPLICATION

This application is a Continuation-In-Part of copending U.S. patent application Ser. No. 10/070,349, filed on Feb. 28, 2002, entitled "Oral Appliance", which in turn is a 371 of PCT/AU99/00840, filed Sep. 29, 1999, claiming priority from Australian patent application Nos. PP 7743 and PQ 1386, filed Dec. 16, 1998 and Jul. 2, 1999, respectively.

FIELD OF THE INVENTION

This invention relates to an oral or mouth appliance and to a method of making the appliance.

This invention relates particularly but not exclusively to an oral appliance that is a sports guard for protecting the teeth of a user in contact sports such as boxing, football, gridiron and rugby. It will therefore be convenient to hereinafter describe the invention with reference to this example application. It is to be clearly understood however that the invention is capable of broader application. For example the invention also extends to an appliance that is an orthodontic appliance.

BACKGROUND TO THE INVENTION

Customised sports mouthguards are known. Typically they are made by taking a mould or impression of a user's mouth and then moulding the guard individually from this impression to fit the specific and unique mouth of the user. While these customised guards obviously fit well in the user's mouth, it will be readily understood that this method of making sports guards is expensive as each guard is made to custom fit the user's mouth. Mass produced sports guards often do not produce a close fit and the protection that they provide is reduced as a result. This has limited their acceptance in the market place despite a clear need for an efficacious mass produced sports guard.

A further limitation of existing custom made and mass produced sports guards is that they are relatively soft and they offer only limited protection to the front teeth. If a blow strikes the front of the mouthguard the guard tends to deform so that the brunt of the blow is borne by the front teeth. This makes the front teeth vulnerable to being damaged or dislodged. It would be better if the force was transferred to all the teeth and particularly through to the back teeth that are particularly firmly anchored to the jaw. This makes the front teeth vulnerable to being damaged or dislodged.

Clearly it would be advantageous if a guard could be devised that had the strength and rigidity to transfer the force rearwardly so that the force is spread over all the teeth and particularly the back teeth. Clearly it would also be advantageous if a guard could be devised that had the fit of a custom made guard but that was mass produced and easy to fit in a domestic environment.

It is an object of the invention to provide a sports guard that ameliorates at least some of the shortcomings of the prior art described above.

SUMMARY OF THE INVENTION

According to one aspect of the invention there is provided an oral appliance, comprising:

a base member made of polyethylene having a generally U-shaped form corresponding to the outline of the arch of a user, the base member having inner and outer flanges interconnected by a web that defines at least one channel within which a row of teeth of a user are received; and a continuous layer of thermoplastic material that is EVA that surrounds and encases the base member and attaches to the base member whereby to define a teeth engaging element within each channel, the thermoplastic material being capable of being moulded and shaped to suit the arch and teeth of a user which are received therein by heating to a certain temperature.

Thus the appliance, eg sports guard, comprises a base member of polyethylene which provides a basic shape and rigidity encased within a layer of thermoplastic material EVA. The layer of thermoplastic EVA can be heated to a temperature at which it is soft and formable and then conformed to the shape of the arch and teeth of a user.

Preferably the layer of thermoplastic material extends continuously over the full surface area of the base member providing a full and uninterrupted cover of the base member without any spaces or openings.

The base member confers a suitable level of rigidity on the base member but does have some flexibility in the direction of length of the channel, eg from front to rear thereof, and this enables the guard to accommodate arches of varying width. In addition it exhibits a surprising level of affinity for the layer of EVA thermoplastic material that covers the base member. This bonding of the EVA layer to the polyethylene together with encasement of the base member within the layer of EVA provides a guard that resists delamination during use. This is a problem that has plagued previous efforts to use thermoplastics materials such as EVA in a mouth appliance.

The applicant has been the first to discover the surprising and unexpected affinity and compatibility that polyethylene has for EVA. The materials have the ability to flex in harmony with each other without delamination. They also remain together when subjected to some level of heating and cooling, eg to shape the EVA. The applicant has also been the first to come up with the idea of encasing the polyethylene base member in the EVA layer. Previously it was thought that satisfactory bonding of an EVA layer to a base member could only be achieved for applications that require some flexing by having a thermoplastic material as the base member, albeit of higher softening point than the EVA layer. The belief was that thermoplastic material would only be compatible with other thermoplastic material.

Typically the layer of EVA softens at a temperature of 90° C. to 95° C., eg by placing it in a glass of boiling water which is available in any domestic or office environment. The layer of thermoplastic material can then be shaped by placing it in the mouth of a user while it is still malleable and formable and then allowing it to set by letting it cool back to room temperature.

The layer of thermoplastics material may have a thickness of 1 mm to 4 mm, preferably 1 mm to 3 mm, eg about 2 mm.

A layer of thermoplastic material of this thickness ensures that the appliance is not overly bulky. When received in a user's mouth it is possible for the user to talk reasonably easily. This is important as in many sports such as football users are required to talk to each other while playing.

The appliance may define only a single said channel that is an upper channel configured to fit over only the upper arch of the user and receive the upper teeth therein. Guards that receive only the upper arch and teeth are the most commonly used sports guards used around the world in contact sports.

Alternatively the appliance may define both an upper and a lower said channel that are configured to fit over the upper and lower arches of a user. Further alternatively the appliance may define a lower said channel configured to fit over only the lower arch of a user. However these configurations are less widely used than the upper arch guards described above.

The web of the base member may thicken in a direction rearwardly along each side thereof from the leading end or front of the base member. Preferably the web thickens in a direction rearwardly to a point spaced a short distance from the rear of the base member and then thins from the point to the rear end. This thickening fills in the space between the upper and lower teeth in an appliance with both upper and lower channels.

The appliance may include a tongue tag, eg centrally positioned, defined in the inner flange for correctly positioning the tongue of a user during use.

Further the appliance may define breathing apertures passing through the base member and layer towards the front of the appliance and broadly centrally in the appliance.

According to another aspect of this invention there is provided a method of making an oral appliance, the method including:

moulding a base member from polyethylene in a first moulding step in a first mould, the member having a generally U-shaped form corresponding to the outline of the jaw of a user and inner and outer flanges interconnected by a web that defines at least one channel within which an arch and associated row of teeth of a user are received; and removing the base member from the first mould and placing it in a second mould having a larger cavity than the first mould and moulding a continuous layer of thermoplastic material that is EVA onto the base member so that the base member is encased by and enclosed within the EVA to form a teeth engaging element that can be formed and shaped to suit the mouth of a user, the layer encasing the polyethylene base member and being compatible therewith to form an integral body that resists delamination during use.

Thus the base member made of polyethylene is moulded in a first moulding step and then the layer of EVA is moulded onto the base member in a second moulding step. It is important that the polyethylene base member has sufficient rigidity not to move when it is exposed to moulding forces in the second moulding step. Applicant has found that polyethylene has sufficient rigidity to withstand the forces of the second moulding step. At the same time it has the rigidity to perform its function in use as a sports guard. It does however permit some flexibility in a longitudinal direction to accommodate user's having arch sizes of varying width.

In a particularly preferred form the base member defines an upper channel within which the upper teeth of a user are received.

The first and second moulding steps may each comprise injection moulding processes. The base member may be injection moulded in a first die or mould defining the shape of the base member. Thereafter the base member is removed from the first die or mould and held in a specific position is a second mould or die defining the shape of the layer of EVA on the base member. It is important that the base member be held firmly in a stationary position in the die for the layer to be successfully moulded onto it. It is also important that the base member is sufficiently rigid not to flex or bend when it is exposed to the pressure of injection moulding the layer.

The second die or mould may include positioning elements such as pins that hold the base member securely in position.

DETAILED DESCRIPTION OF THE PREFERRED EMBODIMENT

An oral appliance in accordance with this invention may manifest itself in a variety of forms. It will be convenient to hereinafter describe in detail several preferred embodiments of the invention with reference to the accompanying drawings. However it is to be clearly understood that the specific nature of this description does not supersede the generality of the preceding broad description of the invention. In the drawings.

Figure 1:
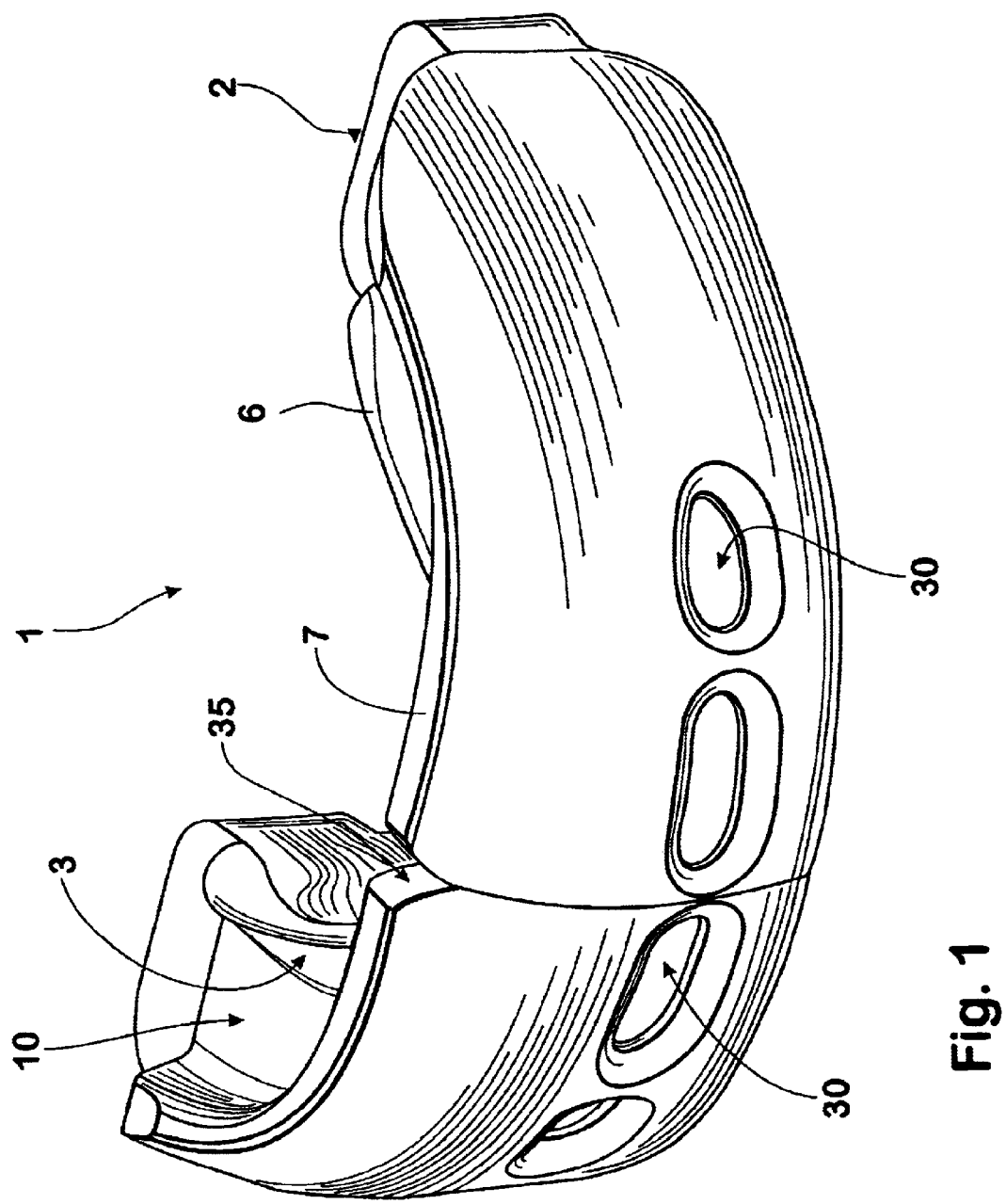
FIG. 1 is a front three dimensional view of an oral appliance in accordance with one embodiment of the invention.
Figure 2:
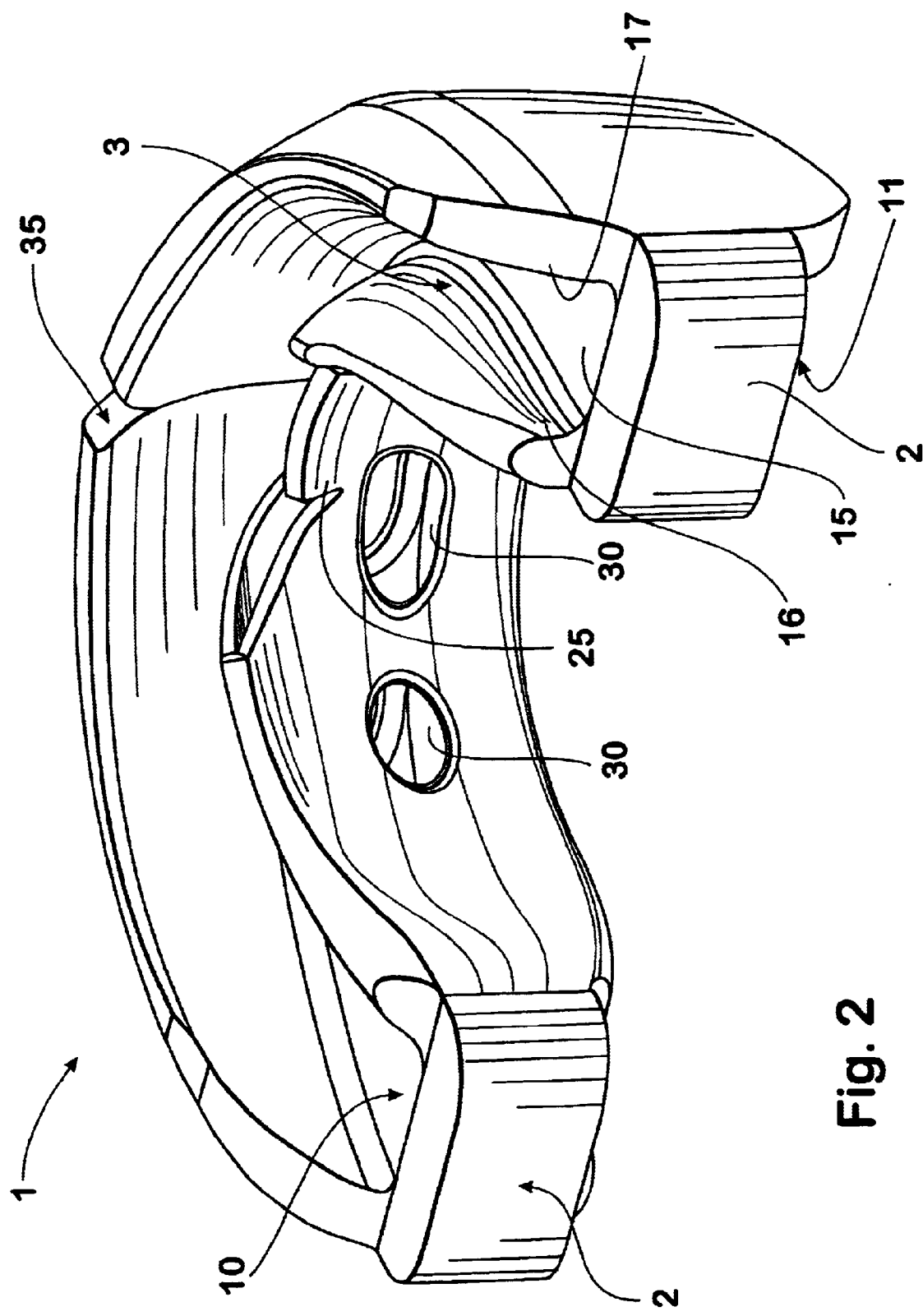
FIG. 2 is a rear three dimensional view of the oral appliance of FIG. 1.
Figure 3:
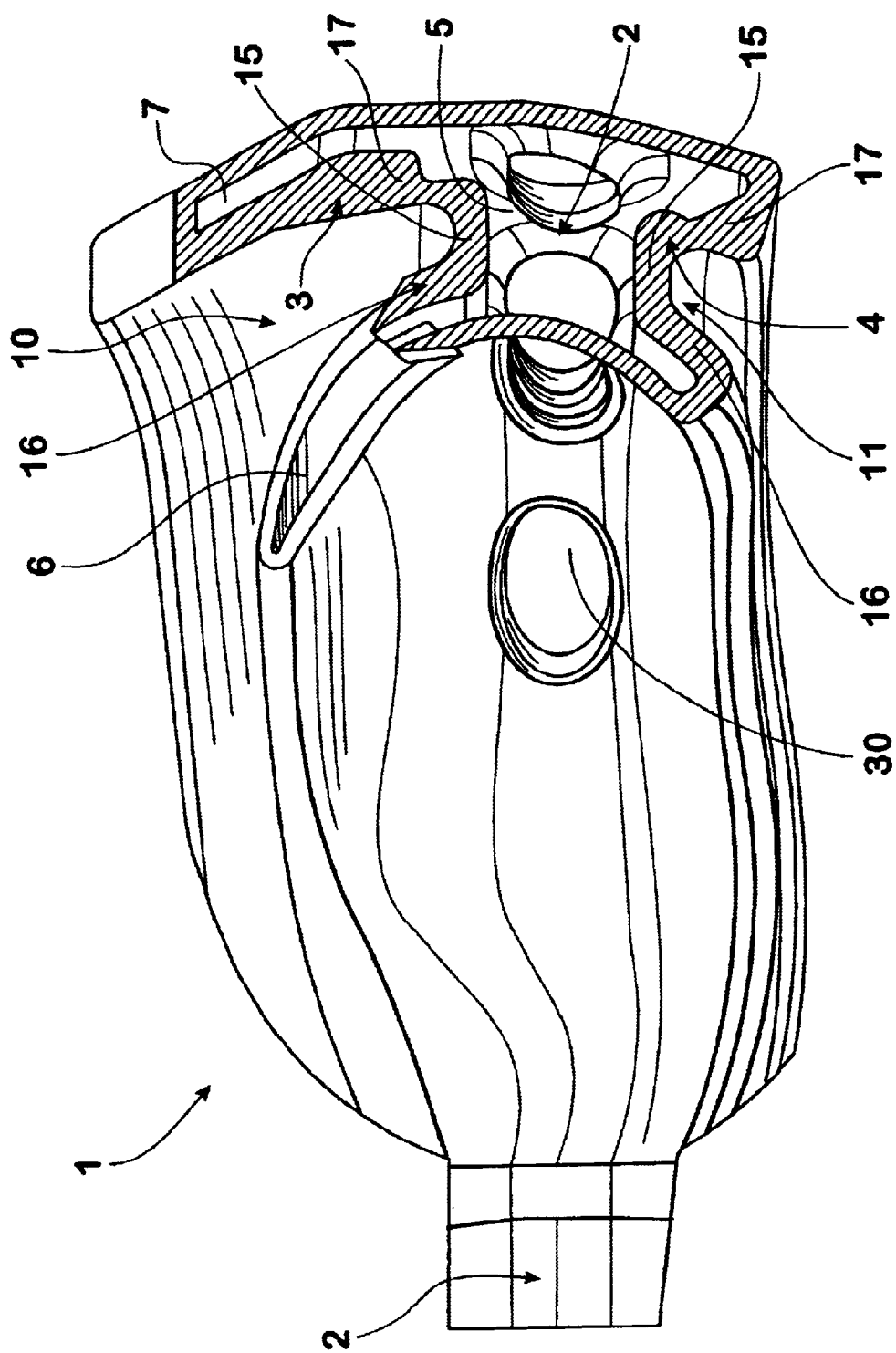
FIG. 3 is a part sectional side view of the appliance of FIG. 1.
Figure 4:
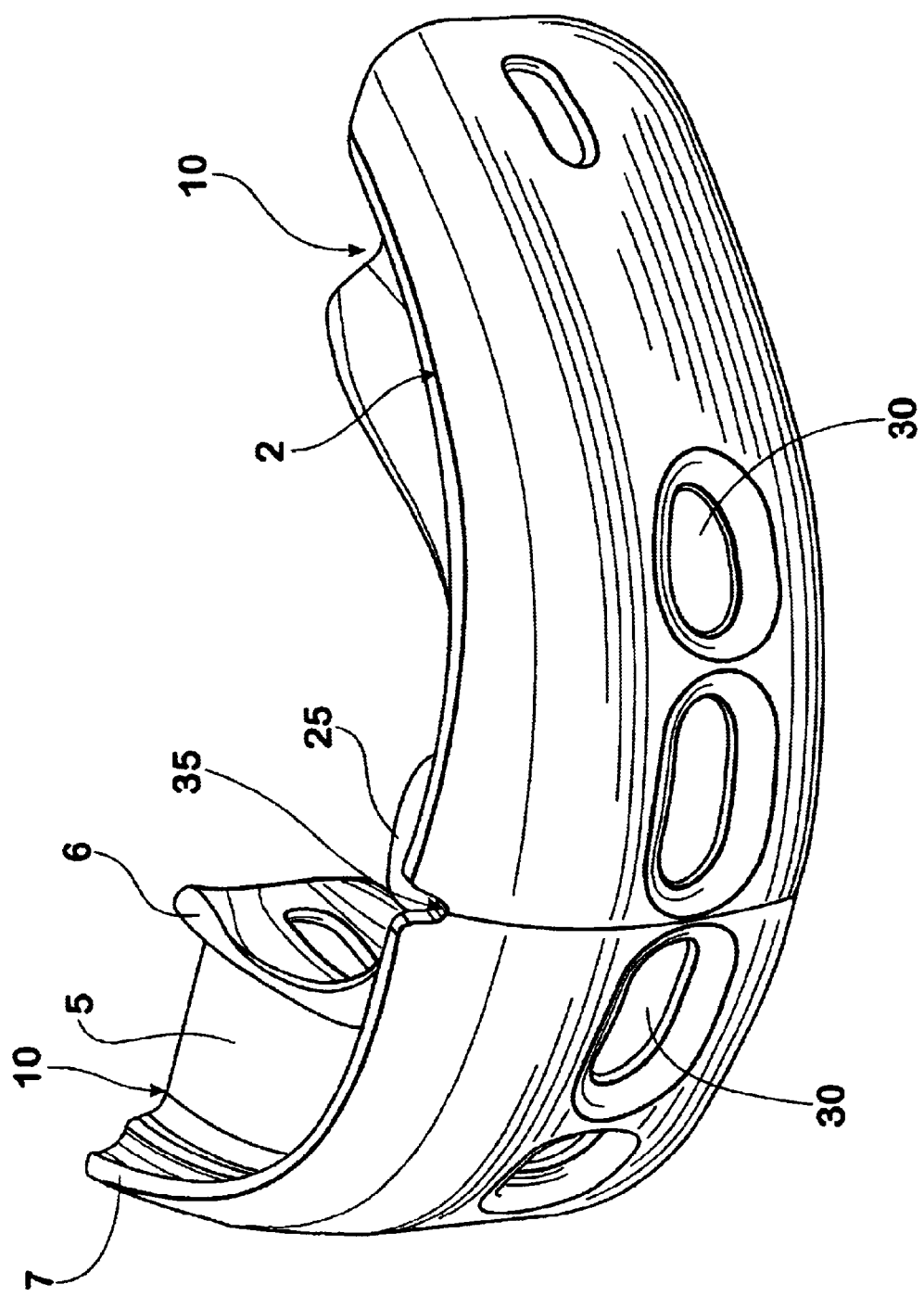
FIG. 4 is a front three dimensional view of the base member of the appliance of FIG. 1.

In FIGS. 1 to 4 reference numeral 1 refers generally to an appliance which may be a sports mouthguard in accordance with the invention.

Figure 12:
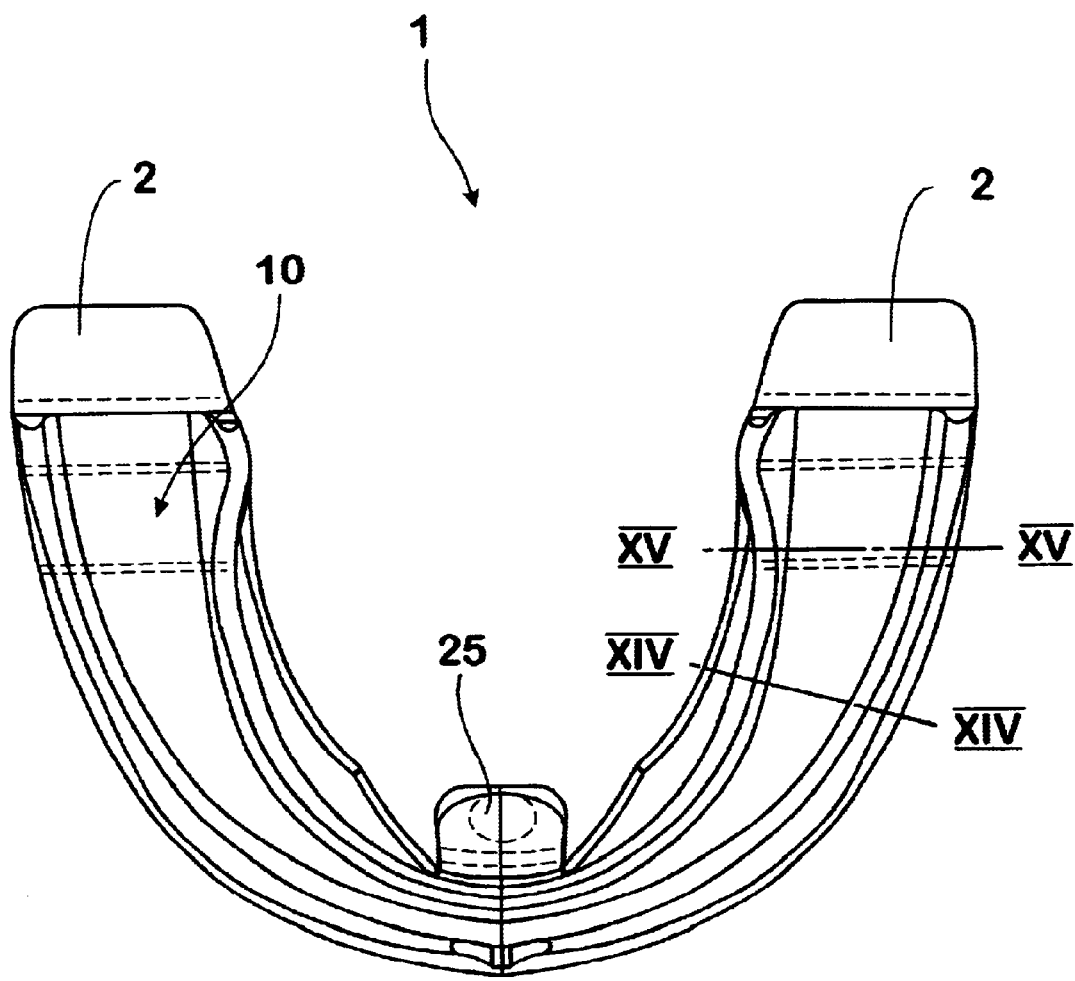
FIG. 12 is a top plan view of an appliance that is a sports guard for fitting over the upper arch of a user.
Figure 13:
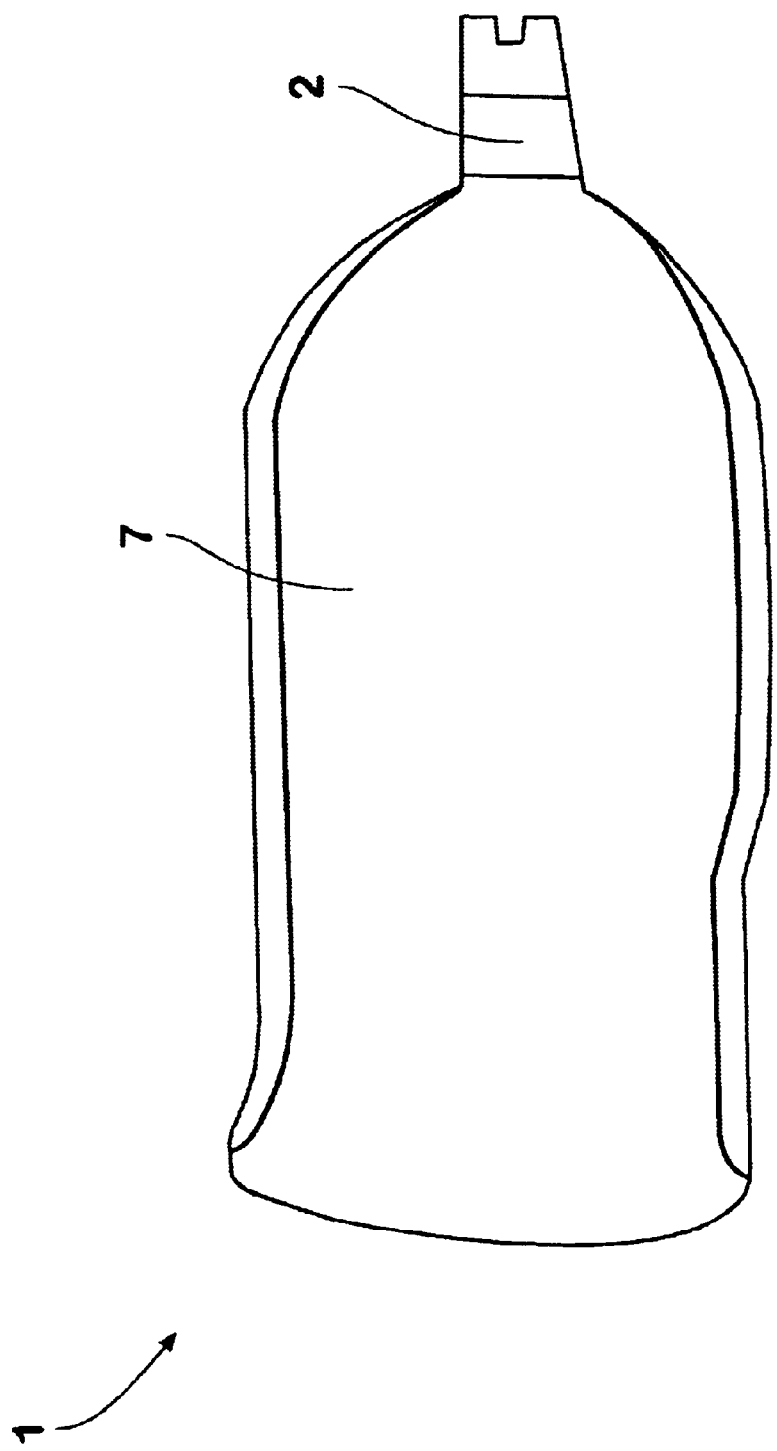
FIG. 13 is a side view of the appliance of FIG. 12.
Figure 14:
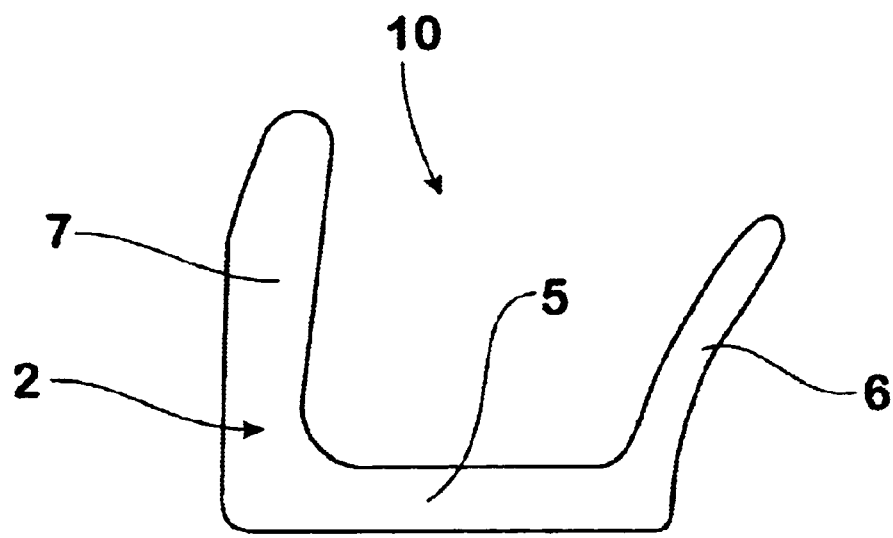
FIGS. 14 and 15 are sectional views through a section of a base member of the appliance, sections through XV—XV and XVI—XVI.
Figure 15:
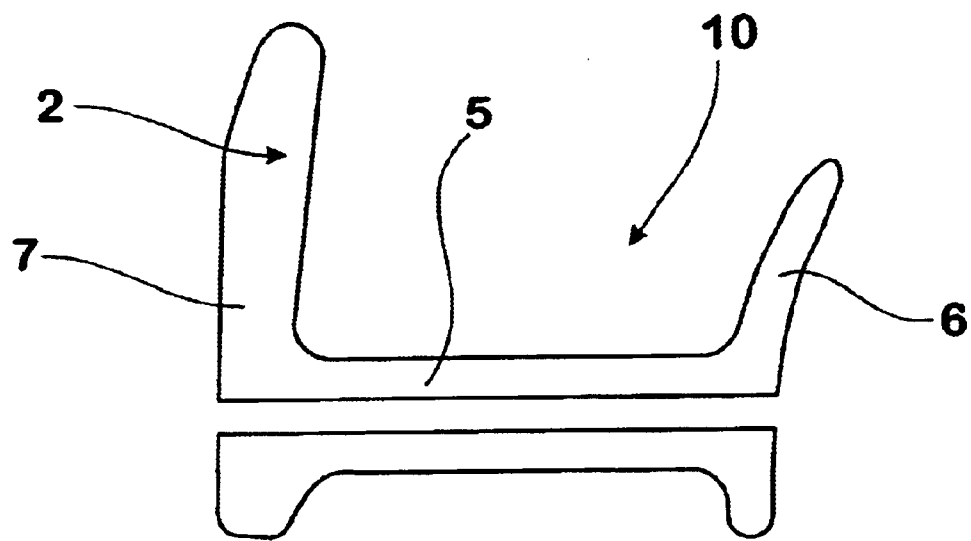

The guard 1 comprises broadly a base member 2 having teeth engaging elements 3, 4 mounted on upper and lower surfaces of the member 2. This embodiment is thus a double arch appliance. A single arch guard that fits over the upper teeth will be described below with reference to FIGS. 12 to 15.

The base member 2 has a broadly U-shaped configuration to complement the U-shape of the arch of a user. The base member 2 has a central web 5 and inner and outer flanges 6 and 7 projecting upwardly and downwardly from both the inner and outer edges of the web 5. The web 5 and the flanges 6 and 7 collectively define upper and lower channels 10 and 11 within which respectively the upper and lower teeth engaging elements 3 and 4 are positioned.

The base member 2 is made of a substantially rigid plastics material that is polyethylene. This has a suitable level of rigidity while still permitting some limited flexing, ie to accommodate the different width of arches for different users.

The teeth engaging elements 3, 4 are formed by a layer of thermoplastics material that is EVA (ethyl vinyl acetate) that encloses and encapsulates the base member 2. The layer has a thickness of 1 mm to 3 mm, typically about 2 mm. EVA has the property that it softens when it is heated to 90° C. to 95° C. This enables it to be shaped to conform to the arch and teeth of a user as will be described in more detail below.

In the illustrated embodiment the layer of EVA extends fully across the surface area of the base member and encases the base member continuously without any interruption, ie without any gaps or spaces.

The EVA appears to have some positive attachment to the polyethylene of the base member. Further the attachment of the layer of EVA to the base member is enhanced by the fact that it encases the base member continuously and extends across the full surface area of the base member. This helps to resist delamination of the two materials during of the appliance.

Each of the tooth engaging elements 3, 4 also has a broadly U-shaped configuration when viewed in plan view. This complements the general shape of the base member 2. Each element 3, 4 also has a broadly U-shaped cross-sectional configuration with a bottom wall 15 and two side walls 16 and 17. The shape and width of the channels defined in the base member 2 and elements 3, 4 have been specifically designed so as to enable the appliance to accommodate widely varying jaw widths and thereby be capable of being fitted to a large number of patients.

The appliance also includes a notch or cut-out 35 in the upper surface of the outer flange 7. The notch 35 has the important function of permitting inward or outward adjustment of the arms of the U-shaped member without causing distortion of the appliances 10. This enables a single appliance to fit patients with different arch sizes.

The guard has a tongue tag for positioning the tongue of a user in a central position during use. The guard also has a number of holes defined therein in the central region thereof that permit mouth breathing by a user. This is often required when playing sports.

A further feature of the guard is that the web of the member thickens from the front of the member to a point towards the rear of the base member just prior to the rear of the member. After this point the member starts thinning down again. This tends to fill in the space between the teeth of the upper and lower jaw. This in some respects resembles an aerofoil and thickens the member. This feature is described in detail in the applicant's earlier U.S. Pat. Nos. 5,259,762 and 5,624,257, the contents of which are incorporated directly herein by cross reference.

The guard is injected moulded in a two-stage injection moulding process. The base member is injection moulded in a first die from polyethylene. The base member is then removed from the first die and locked into a second die in which the EVA layer is injection moulded onto the base member. The base member is held in position by locking elements which are pins. It is particularly important that the base member does not move or flex when the layer of EVA is injection moulded onto it. The base member described above has been found to fully satisfy these requirements.

In use, the sports guard may easily be fitted in a domestic environment. This is done by immersing the guard in boiling water which causes the EVA to soften. Typically, this only takes a few minutes. The base member remains rigid at this temperature. Thereafter the guard is placed in the user's mouth where it moulds and conforms to the arch and teeth of the user's mouth. As it cools to body temperature in the mouth of the user it hardens in the shape that it is forced into and is therefore customised to snugly fit in the mouth of a user.

During actual use of the sports guard it will be subjected to bending and twisting that will tend to cause delamination of the layer and member if they are not firmly attached together. The guard resists delamination when this custom fitting operation is carried out and also later on when the appliance is used. The features that achieve this are the encasement of the base member within the layer and the compatibility of polyethylene within EVA. These two materials bend and flex together with comparable degrees of elasticity and extension.

The layer of EVA is relatively thin so the guard is not excessively bulky in a user's mouth. This is an important feature that enables users to talk while they are wearing the guard. Talking is an important part of playing some contact sports.

Figure 5:
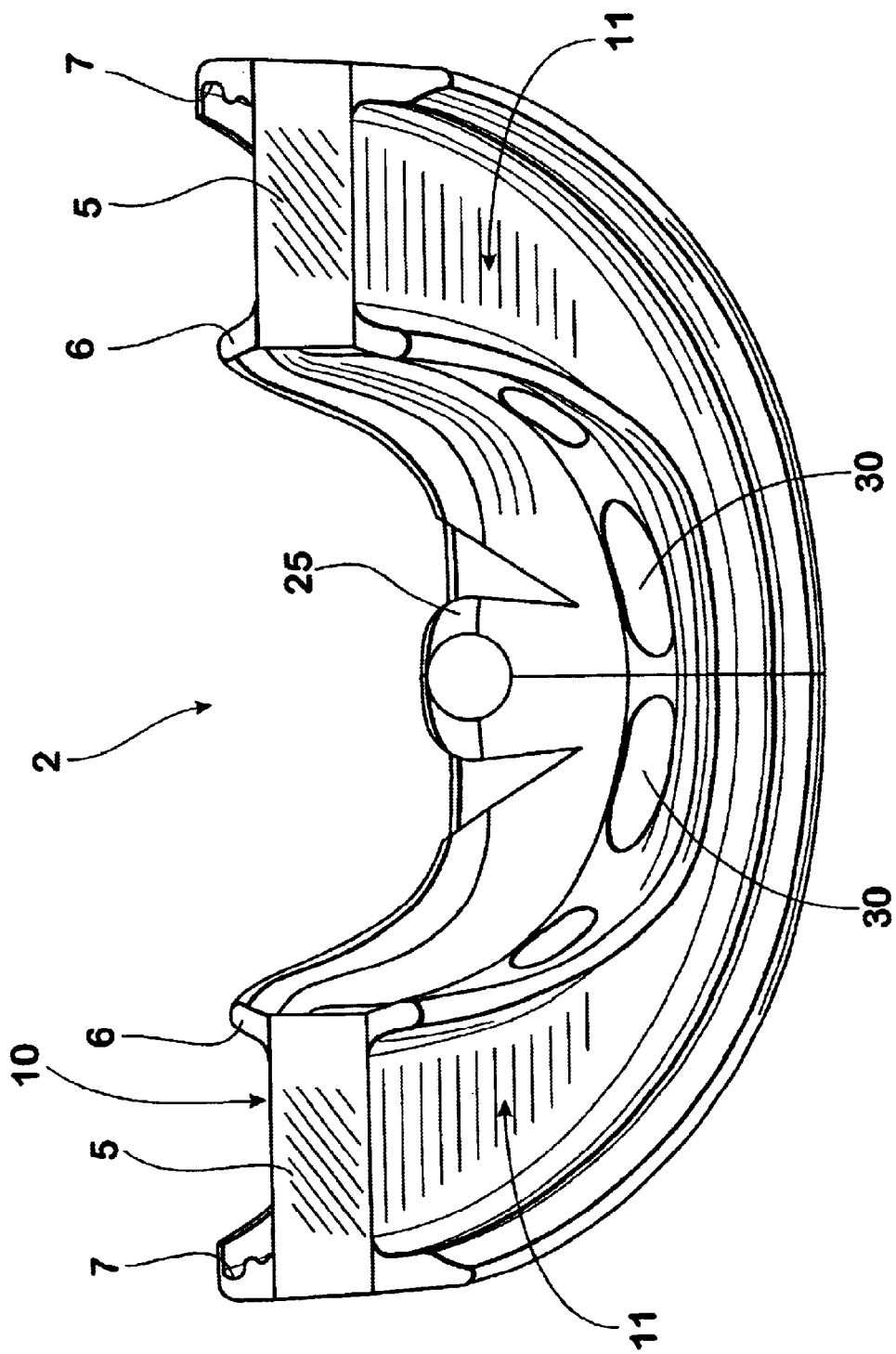
FIG. 5 is a rear three dimensional view of the base member of FIG. 4.
Figure 6:
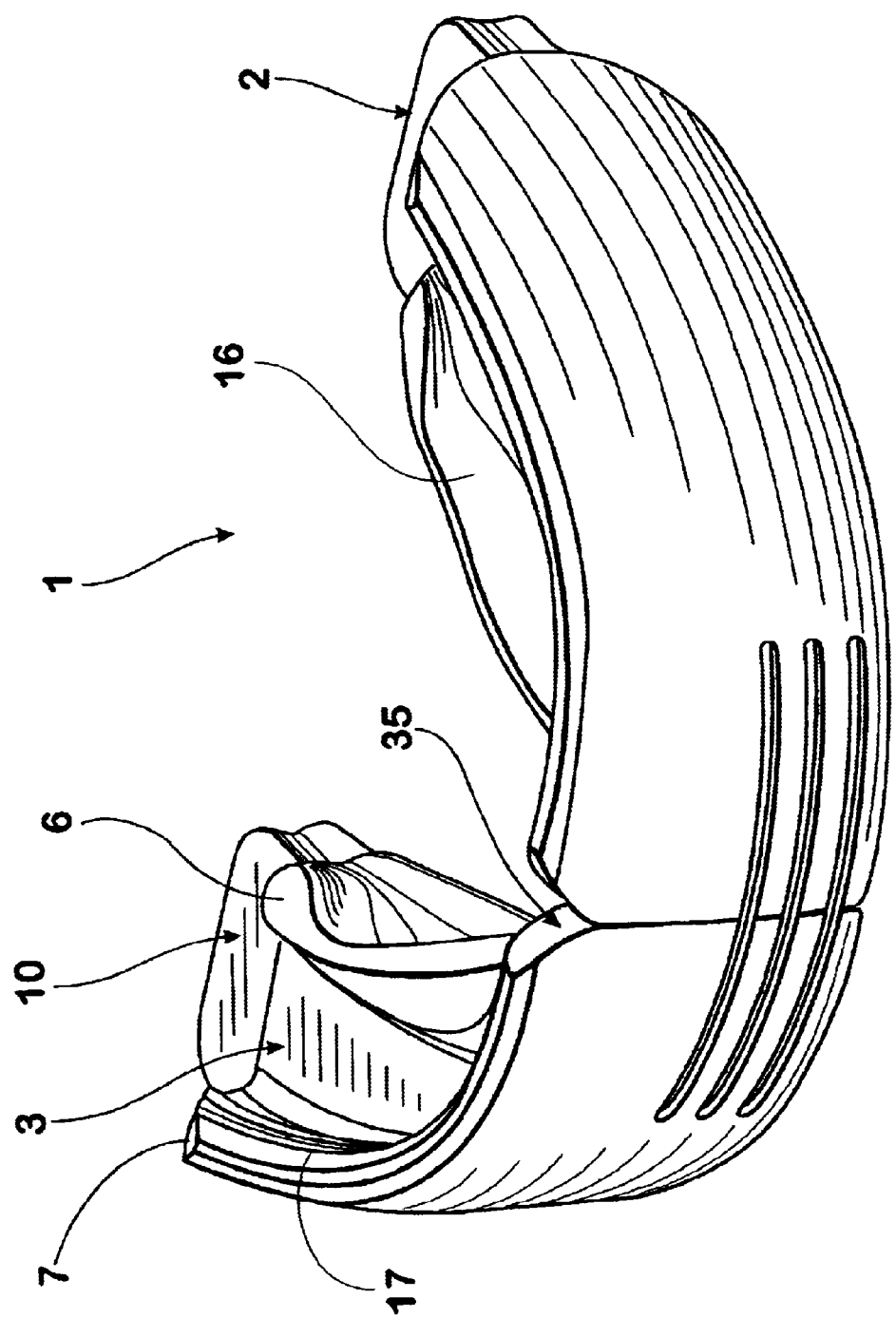
FIG. 6 is a front three dimensional view of an appliance in accordance with a second embodiment of the invention.
Figure 7:
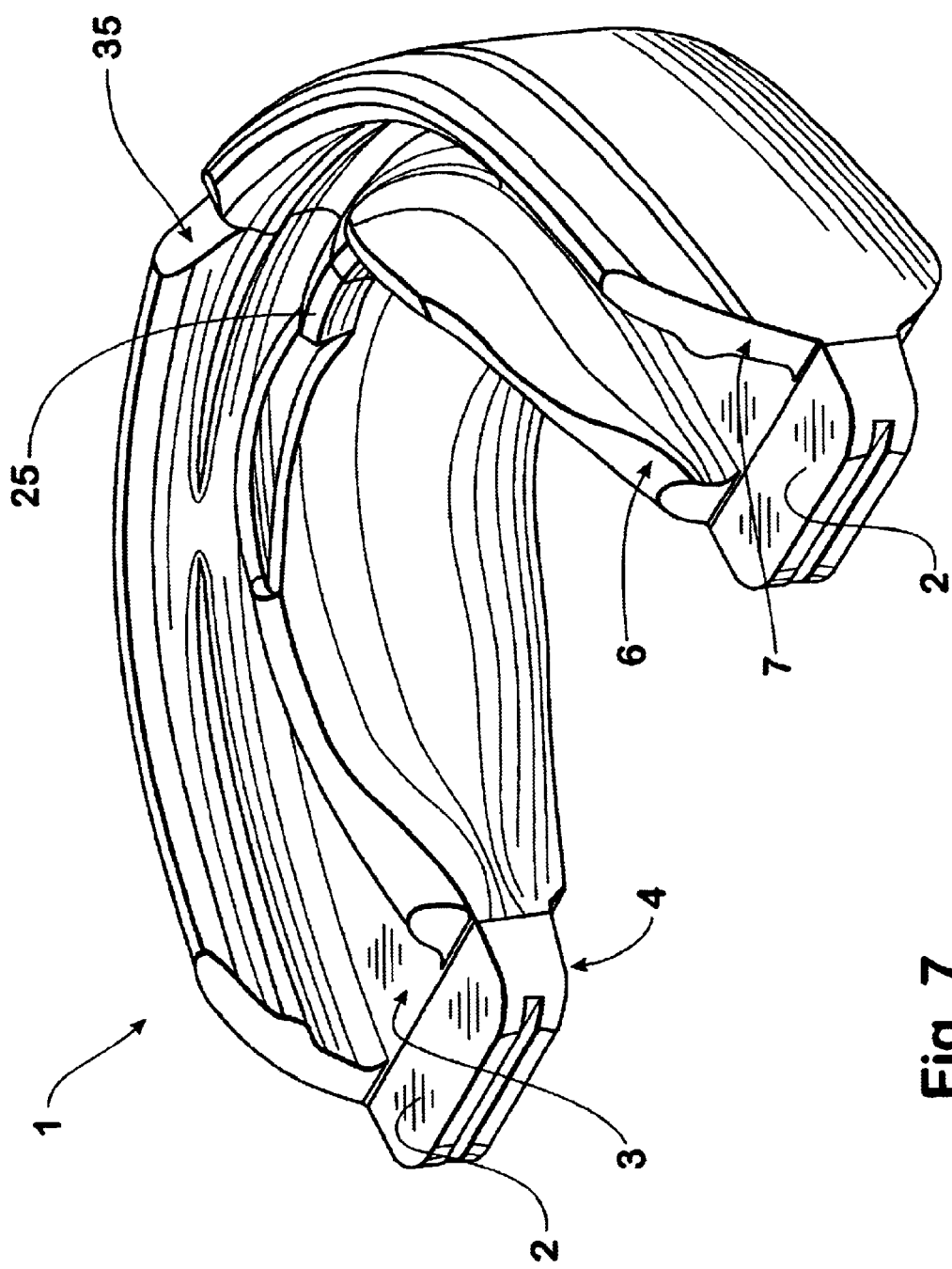
FIG. 7 is a rear three dimensional view of the appliance of FIG. 6.
Figure 8:
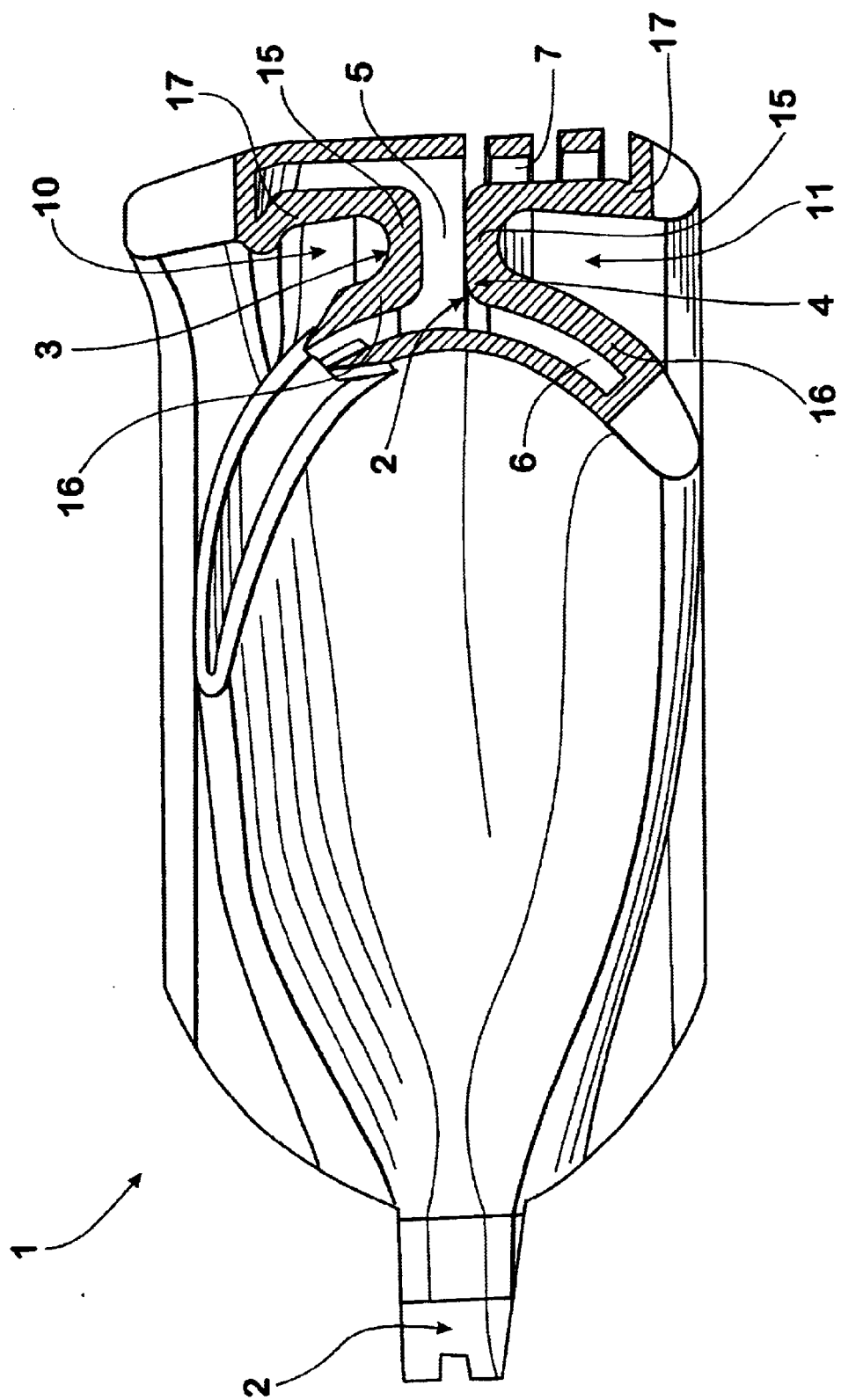
FIG. 8 is a part sectional side view of the appliance of FIG. 6.
Figure 9:
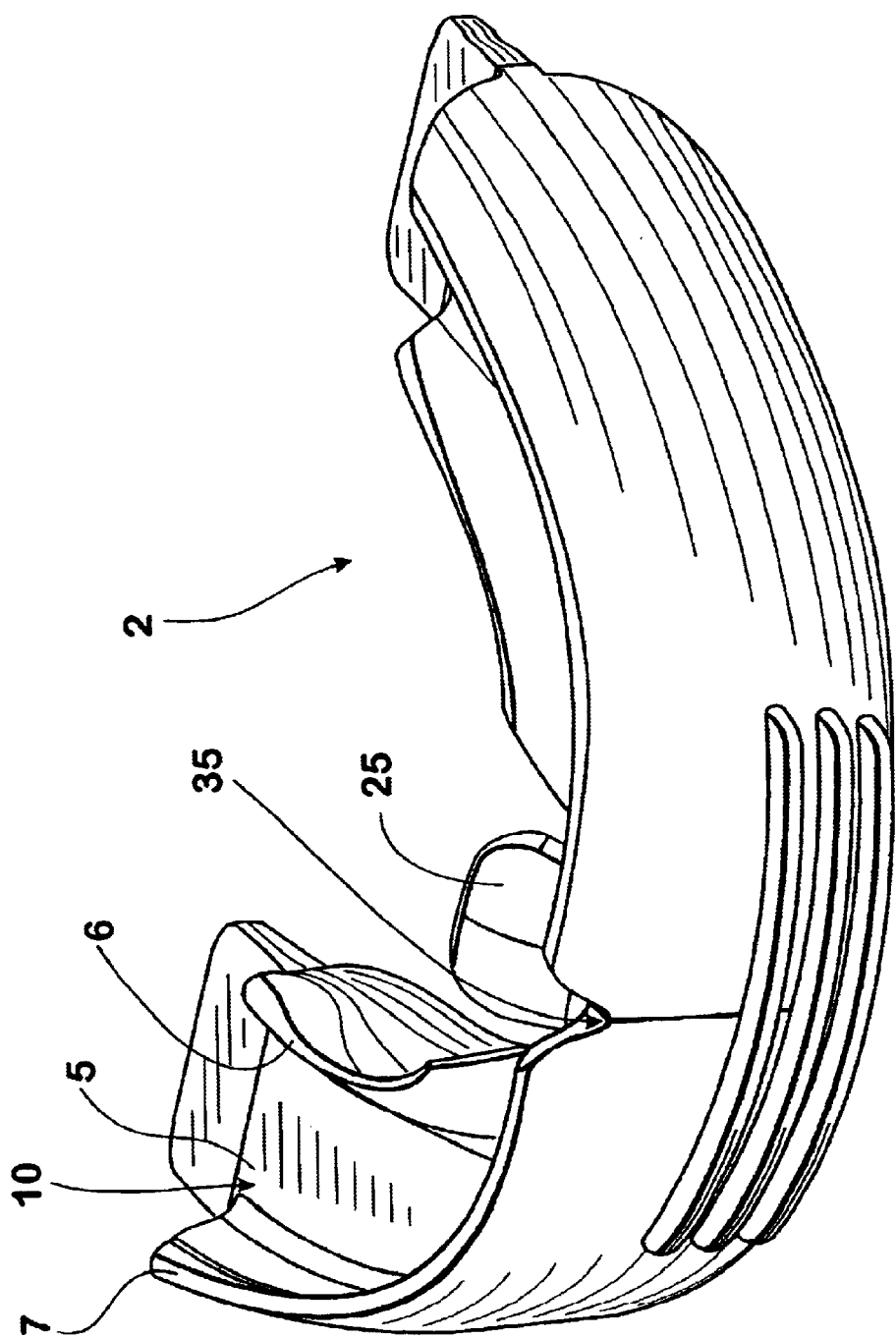
FIG. 9 is a front three dimensional view of the base member of the appliance of FIG. 6.
Figure 10:
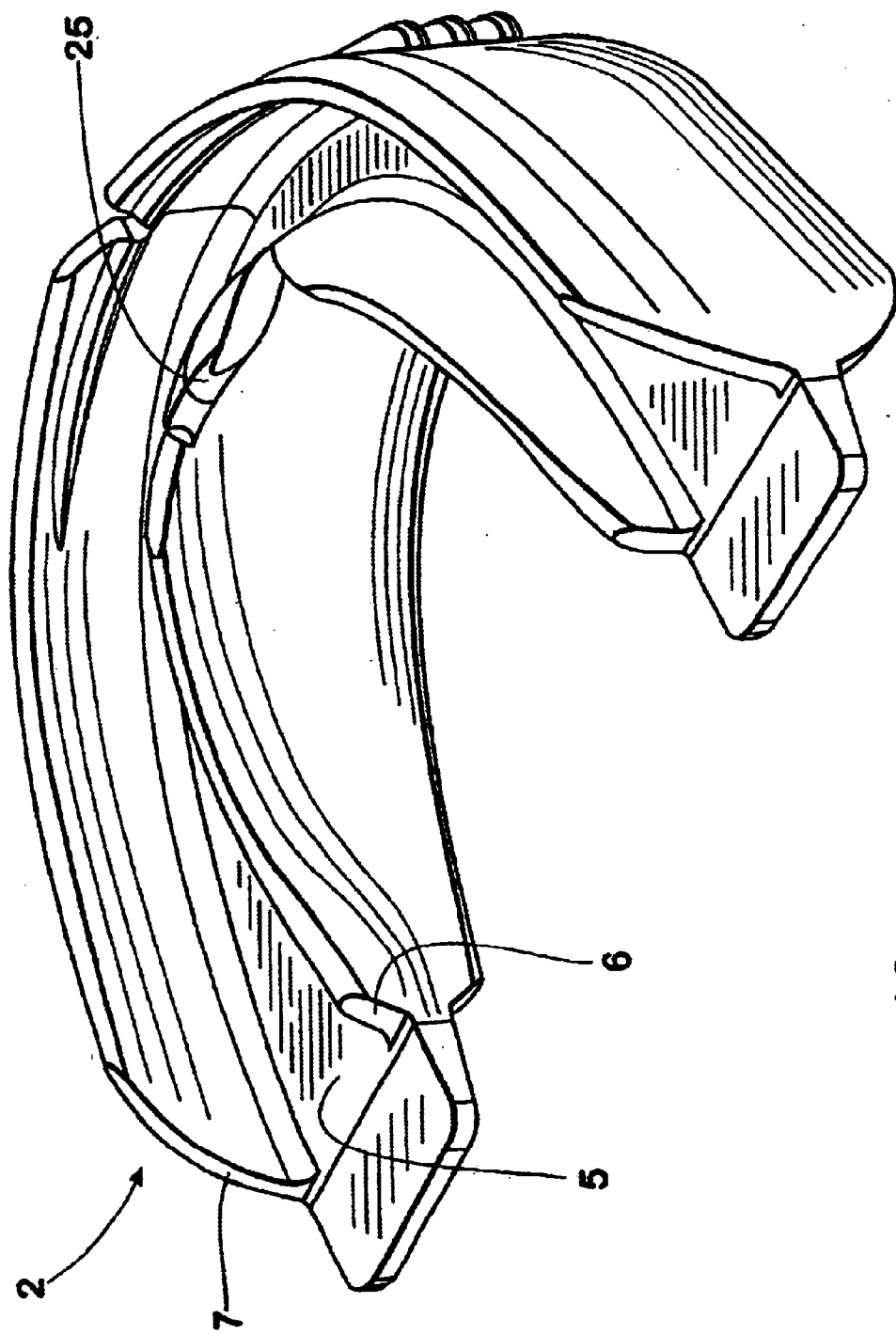
FIG. 10 is a rear three dimensional view of the base member of FIG. 9.
Figure 11:
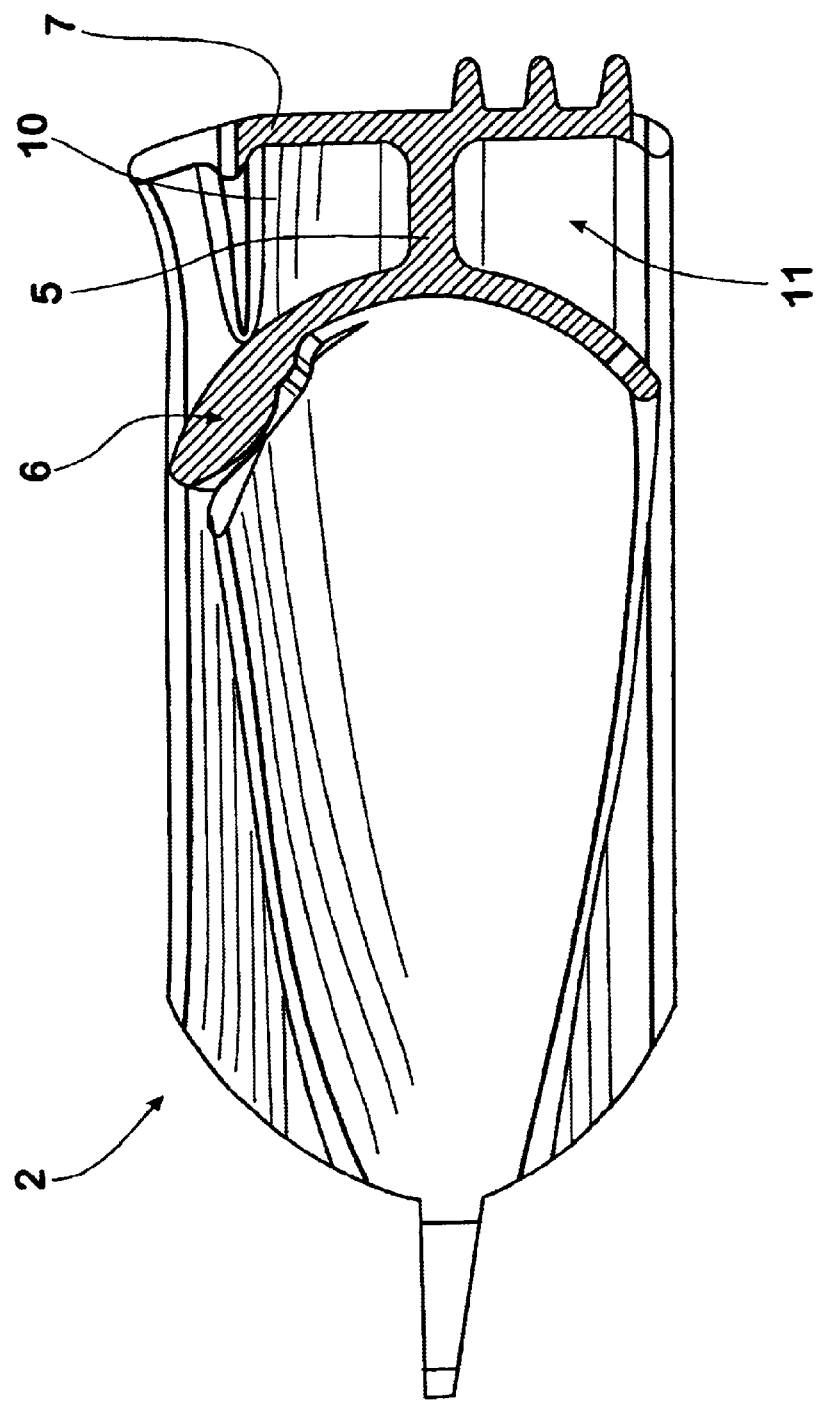
FIG. 11 is a sectional side view of the base member of FIG. 9.

In a second embodiment of the invention illustrated in FIGS. 5 to 11, the appliance is used for orthodontic treatment. The orthodontic appliance is the same as that illustrated in FIGS. 1 to 5 with the exception that it does not have breathing holes, eg for mouth breathing, and the base element 2 is thinner, eg having an approximate thickness of 2 mm to 4 mm, because it does not have the same requirements of mechanical strength as the sports guard. The orthodontic appliance is used for myofunctional training and tooth alignment. Myofunctional training is a clinical procedure which is designed to correct bad oral habits, eg tongue thrusting, mouth breathing, incorrect swallowing and the like.

In use the appliance is initially fitted by a dentist or orthodontist in a dental surgery. The shape of the elements 3, 4 prior to use corresponds broadly to an ideal positioning or "bite" of a patient's teeth. To enable the elements 3, 4 to be tailored to a patient's specific teeth, the elements 3, 4 are dipped into boiling water to soften the elements and then inserted into a patient's mouth to mould them to the specific contours of a patient's mouth.

The EVA material from which the elements 3, 4 are formed has a memory so that it reverts to its original shape when reheated. It reverts partly to its original shape when heated to 60° C. to 65° C. and fully to its original shape when heated above 90° C.

The memory properties of the EVA enable the elements 3, 4 to be used to progressively correct misalignment of a patient's teeth. For example at spaced time intervals, the dentist will typically place the appliance into water at a temperature of 60° C. to 65° C. which causes the elements 3, 4 to partly revert to their original shape. The slightly altered shape brought about by this remoulding causes the appliance to apply pressure to the teeth of a user to correct misalignment. This can be done several times until the patient's teeth take up the correct position or the ideal "bite" position.

When the teeth are in the correct position the appliance can be placed into water at 90° C. to 95° C. which causes it to revert to its original position. The appliance can then be used as a retaining device for retaining the teeth in the correct position and also for carrying out myofunctional training.

FIGS. 12 to 15 illustrate an appliance in accordance with a second embodiment of the invention that is a sports guard. Unless otherwise indicated the same reference numerals will be used to indicate the same components. The major difference between this embodiment and the earlier embodiment is that this embodiment only defines an upper channel within which the upper arch of a user is received. The guard would generally be used in contact sports where it acts to resist damage to the teeth and jaw of a user. In particular the guard protects the vulnerable front incisor teeth and the temporo-mandibular (TMJ) joint of a user.

Subject to these differences the sports guard comprises the same structural features as the appliance illustrated in FIGS. 1 to 11. It comprises a base member made of polyethylene that is encapsulated in a layer of EVA material. The EVA material is softened by placing it in hot water and then placed in a user's mouth to shape it to the arch and teeth of a user.

This process of moulding the guard to fit the teeth and arch of a user involves heating the guard up and then cooling it down. Applicant has found that polyethylene and EVA are compatible with each other when undergoing this process and do not delaminate. Further when the appliance is subjected to flexing in use the polyethylene and EVA are able to flex together and resist delamination.

Without being bound by theory Applicant believes that the levels of thermal expansion of the materials are compatible with each other. Also the ability of the materials to flex or stretch at their interfacing surfaces is comparable.

An advantage of the sports guard described above is that when the guard is heated in water it does not change or lose its basic shape. This is because the base member is sufficiently strong and rigid to resist this. The hard base member forces the layer of thermoplastic material against the teeth where it conforms to the contours of the teeth. These guards which are essentially mass produced and are one size fits all produces an excellent fit that is comparable to that achieved with custom made guards produced by taking impressions of a user's mouth and jaw.

A further advantage of the guard described in this application is that it can be remoulded to maintain optimum fit should the fit become loose for any reason. The guard is simply heated again in boiling water and then returned to the mouth of the user where it is reshaped to restore optimum fit. Prior art custom made sports guards of which the applicant is aware are not able to do this.

A further advantage of the guard described above is that it has the ability to spread the force from a blow or impact to the front of the guard across the full body of the guard. It does this because the base member is sufficiently rigid not to deform locally when such an impact occurs. Rather the entire guard absorbs the impact and tends to move in response thereto. By spreading the force over the entire mouth of a user rather than the fragile front teeth, the risk of injury to the front teeth is considerably reduced. The rear molars have a number of extensive roots and are thicker and more robust than the front teeth. They are therefore better adapted to withstand a strong blow to the mouth. Many prior art sports guards do not have this ability. They tend to bend or deform locally in response to a frontal impact, transferring the force of the blow directly to the front teeth.

A further advantage of the guard described above is that the web has an aerofoil shape on each side of the arch extending from the front towards the rear of the arch. Both the base member has an aerofoil shape beneath the thermoplastic layer and the thermoplastic layer also has this shape. The aerofoil fills in the space between the upper and lower teeth and provides support to the TMJ joint. Applicant believes that this feature assists in transferring the shock of a blow to the front of the jaw to all the teeth and from the teeth through to the skull, rather than concentrating the impact at the TMJ which can damage this joint. The rigid base member that cannot easily be deformed provides an appropriate level of support to the TMJ joint.

It will of course be realised that the above has been given only by way of illustrative example of the invention and that all such modifications and variations thereto as would be apparent to persons skilled in the art are deemed to fall within the broad scope and ambit of the invention as herein set forth.

What is claimed is:

1. An oral appliance comprising:
    a base member made of polyethylene having a generally U-shaped form corresponding to the outline of the arch of a user, the base member having inner and outer flanges interconnected by a web that defines at least one channel within which a row of teeth of a user are received; and
    a continuous layer of thermoplastic material that is EVA that surrounds and encases the base member and attaches to the base member whereby to define a teeth engaging element within each channel, the layer being capable of being moulded and shaped to suit the arch and teeth of a user by heating to a certain temperature.

2. An oral appliance according to claim 1, wherein the layer of thermoplastic material extends continuously over the full surface area of the base member, providing a full and uninterrupted cover over the base member.

3. An oral appliance according to claim 2, wherein the layer of thermoplastics material has a thickness of 1 mm to 3 mm.

4. An oral appliance according to claim 3, wherein the appliance is a sports guard and the sports guard defines only a single said channel that is an upper channel configured to fit over the upper arch of the user and receive the upper teeth therein.

5. An oral appliance according to claim 1, wherein the web of the base member thickens in a direction rearwardly along each side thereof from a front of the base member to a point spaced a short distance forward of the rear of the base member, and then the base member thins in a direction rearwardly from said point to the rear end.

6. A method of making an oral appliance, the method including:
    moulding a base member from polyethylene in a first moulding step in a first mould, the member having a generally U-shaped form corresponding to the outline of the jaw of a user and inner and outer flanges interconnected by a web that defines at least one channel within which an arch and associated row of teeth of a user are received; and
    removing the base member from the first mould and placing it in a second mould having a larger cavity than the first mould and moulding a continuous layer of thermoplastic material that is EVA onto the base member so that the base member is encased by and enclosed within the EVA to form a teeth engaging element within each channel that can be formed and shaped to suit the mouth of a user, the layer encasing the base member and bonding to the base member to form an integral body that resists delamination during use.

7. A method according to claim 6, wherein said base member defines only one said channel which is an upper channel within which the upper teeth of a user are received.

8. A method according to claim 6, wherein the base member of polyethylene is moulded in a first injection moulding step in a first die or mould defining the shape of the base member, and thereafter the base member is removed from the first die or mould and then the base member is placed in a second mould or die defining the shape of the layer of EVA, and the layer of EVA is then injection moulded in said second die or mould, and then the moulded appliance is ejected from the second die or mould.

9. A method according to claim 8, wherein the base member is held in said specific position in the second mould or die by means of positioning elements such as pins such that an even layer of EVA is moulded onto the base member.

* * * * *